(12) United States Patent
Tremellen et al.

(10) Patent No.: US 12,144,824 B2
(45) Date of Patent: Nov. 19, 2024

(54) METHOD FOR ENHANCING EMBRYO IMPLANTATION

(71) Applicants: The Flinders University of South Australia, Bedford Park (AU); The University of Melbourne, Parkville (AU)

(72) Inventors: Kelton Paul Tremellen, Bedford Park (AU); David K Gardner, Parkville (AU); Alexandra J. Harvey, Parkville (AU)

(73) Assignee: NULIFE B.V., Rotterdam (NL)

( * ) Notice: Subject to any disclaimer, the term of this patent is extended or adjusted under 35 U.S.C. 154(b) by 651 days.

(21) Appl. No.: 17/059,221

(22) PCT Filed: May 29, 2019

(86) PCT No.: PCT/AU2019/000067
§ 371 (c)(1),
(2) Date: Nov. 26, 2020

(87) PCT Pub. No.: WO2019/227122
PCT Pub. Date: Dec. 5, 2019

(65) Prior Publication Data
US 2021/0213053 A1     Jul. 15, 2021

(30) Foreign Application Priority Data
May 29, 2018  (AU) ................................ 2018901900

(51) Int. Cl.
| | | |
|---|---|---|
| *A61K 33/34* | (2006.01) | |
| *A61B 17/43* | (2006.01) | |
| *A61B 17/435* | (2006.01) | |
| *A61K 9/06* | (2006.01) | |
| *A61K 9/08* | (2006.01) | |
| *A61K 9/14* | (2006.01) | |
| *A61K 33/30* | (2006.01) | |
| *A61K 47/10* | (2017.01) | |
| *A61K 47/38* | (2006.01) | |

(52) U.S. Cl.
CPC .............. *A61K 33/34* (2013.01); *A61B 17/43* (2013.01); *A61B 17/435* (2013.01); *A61K 9/06* (2013.01); *A61K 9/08* (2013.01); *A61K 9/14* (2013.01); *A61K 33/30* (2013.01); *A61K 47/10* (2013.01); *A61K 47/38* (2013.01)

(58) Field of Classification Search
CPC ... A61K 9/06; A61K 9/08; A61K 9/14; A61K 33/30; A61K 33/34; A61K 47/10; A61K 47/38; A61B 17/43; A61B 17/435
See application file for complete search history.

(56) References Cited

U.S. PATENT DOCUMENTS

| 3,803,308 A | 4/1974 | Zipper |
| 2014/0271919 A1 | 9/2014 | Abbott et al. |
| 2017/0173074 A1 | 6/2017 | Canals Almazán et al. |

FOREIGN PATENT DOCUMENTS

| RU | 2185175 C2 | 7/2002 |
| WO | 2011/059232 A1 | 5/2011 |
| WO | 2016/123539 A1 | 8/2016 |
| WO | 2018/115788 A1 | 6/2018 |

OTHER PUBLICATIONS

Hu et al., "Antifertility effectiveness of a novel copper-containing intrauterine device material and its influence on the endometrial environment in rats", Apr. 12, 2018, Materials Science & Engineering, C 89, pp. 444-455. (Year: 2018).*
Hu et al., Antifertility effectiveness of a novel copper-containing intrauterine device material and its influence on the endometrial environment in rats, Apr. 12, 2018, Materials Science & Engineering C, vol. 89, pp. 444-455. (Year: 2018).*
Goodman LR et al., "Novel approach to recurrent implantation failure: short-term copper intrauterine device placement—Fertility and Sterility", Instituto Valenciano de Infertilidad/Reproductive Medicine Associates, Fertil Steril 108(1):42-43 (2017).
Liang Y et al., "Effect of Endometrial Injury on Secretion of Endometrial Cytokines and IVF Outcomes in Women with Unexplained Subfertility", Mediators Inflamm doi: 10.1155/2015/757184 (2015).
Sahin C et al., "Increased Stem Cell Marker Expressions during the PeriImplantation Period in the Rat Endometrium: Constructive Role of Exogenous Zinc and/or Progesterone", Biomed Res Int doi: 10.1155/2014/867131 (2014).
Tawfeek MA et al., "Assessment of leukemia inhibitory factor and glycoprotein 130 expression in endometrium and uterine flushing: a possible diagnostic tool for impaired fertility", BMC Women's Health 12:10 (2012).

(Continued)

*Primary Examiner* — Ali Soroush
(74) *Attorney, Agent, or Firm* — N.V. NEDERLANDSCH OCTROOIBUREAU

(57) ABSTRACT

A method of enhancing embryo implantation in a subject is disclosed which comprises administering to the uterine cavity of the subject a formulation comprising copper and/or zinc in an amount effective to stimulate endometrial production of leukaemia inhibitory factor (LIF) and/or vascular endothelial growth factor (VEGF). Alternatively, a device may be inserted into the uterine cavity of the subject, wherein the device comprises copper and/or zinc, for a period of time that is effective to stimulate endometrial production of LIF and/or VEGF. The method is suitable for use with women undergoing treatment by any of the assisted reproductive technologies, such as those involving the transfer of embryos such as in vitro fertilisation (IVF) and variants including IVF-ICSI (intracytoplasmic sperm injection) and in vitro maturation (IVM) treatments, as well as intrauterine-insemination (IUI) therapy. However, the method is also applicable for women wanting to improve their prospects of pregnancy through natural conception.

14 Claims, 8 Drawing Sheets

(56) References Cited

OTHER PUBLICATIONS

Mao, X. et al. "Short-term copper intrauterine device placement improves the implantation and pregnancy rates in women with repeated implantation failure" Fertility and Sterility (2018) vol. 8, No. 1, pp. 55-61.
Hu, L.-X. et al. "Biological Evaluation of the Copper/Low-density Polyethylene Nanocomposite Intrauterine Device", PLoS One (2013) vol. 8, No. 9, e74128.
Laudanski, T et al. "Influence of copper ions on uterine activity" Contraception (1981) vol. 24, No. 2 pp. 195-202.
Stephenson, J. L. & Brackett, B. G. "Influences of zinc on fertilisation and development of bovine oocytes in vitro" Zygote (1999) vol. 7, pp. 195-201.

\* cited by examiner

METHOD FOR ENHANCING EMBRYO IMPLANTATION

TECHNICAL FIELD

The present disclosure relates to the field of assisted reproductive technologies such as in vitro fertilisation (IVF). More particularly, the disclosure relates to methods and a formulation and device for enhancing implantation of transferred embryos to a subject.

PRIORITY DOCUMENT

The present application claims priority from Australian Provisional Patent Application No 2018901900 titled "Method for enhancing embryo implantation" filed on 29 May 2018, the content of which is hereby incorporated by reference in its entirety.

BACKGROUND

While huge improvements in IVF treatment over the last three decades have considerably advanced the understanding of how to optimise embryo development in vitro, very little advancement has been made regarding methods for optimising or enhancing the successful implantation of transferred embryos. Even today, the transfer of a good morphology, genetically normal embryo to the uterus of a "fertile" recipient (i.e. a woman with no impediments to her own fertility potential, such as pure male factor infertility) still does not guarantee successful implantation, with up to half of these "top quality" embryos failing to implant (Dahdouh et al., 2015). As such, human IVF can be considered to be very inefficient compared to species such as mice and rabbits where in excess of 95% of embryos successfully implant (Valbuena et al., 2017). Further, many women undertaking IVF treatment undergo the transfer of multiple good quality embryos and never have a successful pregnancy, suggesting a major impediment to implantation in this recurrent implantation failure (RIF) cohort. Moreover, many women are childless because their embryos fail to successfully implant, rather than being incapable of producing embryos (Martin, 1995), which of course implies an underlying implantation deficit.

To date, the only treatment known to augment implantation in RIF is disruption of the endometrium, either by curettage (also known as "endometrial scratching") (Nastri et al., 2015) or the insertion and subsequent removal of a contraceptive intra-uterine contraceptive device (IUCD) (Mao et al., 2017). It is not fully understood how this process enhances implantation, but it has been reported that the inflammatory reaction associated with endometrial disruption causes the release of cytokines and growth factors known to enhance embryo development (Liang et al., 2015). However, these current approaches to treat RIF have several disadvantages. First, they are generally conducted at least one menstrual cycle before the actual embryo transfer, allowing the damaged endometrium to be shed with menses and then time to repair itself—disruption of the endometrium (curettage) in the same menstrual cycle as an embryo transfer has been reported to impair implantation (Karimzade et al., 2010) as anticipated given that this process disrupts endometrial integrity and is associated with significant bleeding within the uterine cavity. Secondly, the process of taking an endometrial biopsy or insertion of an IUCD is painful to the recipient. As such, an ideal therapy would be one that is relatively painless, free of side effects and can be conducted in the same menstrual cycle as the anticipated embryo transfer.

It is presently unclear why human reproduction is less efficient than most other animal species. However, significant inter-species differences in early reproductive events may account for this anomaly, plus provide some insight into how implantation may be enhanced in humans. In prolific breeders such as rodents, rabbits and pigs, the cervix remains open around the time of mating, thereby allowing large volumes of seminal plasma and sperm to bathe the uterine endometrium and initiate the production of growth factors and cytokines, and additionally lead to the generation of a prominent post-mating uterine inflammatory response (Schjenken and Robertson, 2014; Robertson and Sharkey, 2016). This inflammatory reaction to semen remodels the uterine lining, as well as facilitates the growth and development of the embryo. Surgical removal of male accessory sex glands (prostate, seminal vesicle), thereby blocking uterine exposure to seminal plasma, results in a significantly diminished uterine inflammatory reaction and impaired implantation, underlying the reproductive importance of this response (Schjenken and Robertson, supra; Robertson and Sharkey, supra). However, the uterine cavity of women is exposed to a relatively low number of sperm and associated seminal plasma proteins because sperm must pass through the cervical mucous "filter" before reaching the uterus (Schjenken and Robertson, supra). This significantly different reproductive physiology between species means that women's exposure to semen following intercourse has less potential to trigger an inflammatory response capable of augmenting implantation compared to intra-uterine ejaculating animals.

Aside from seminal plasma, other triggers for uterine inflammation have been reported. For example, zinc and copper metal ions are known to be cytotoxic to endometrial cells in culture (Wu et al., 2012), and create an intra-uterine inflammatory response in the context of exposure to an IUCD (Sadovsky et al., 1975; Stanford and Mikolajczyk, 2002). While this IUCD-related endometrial inflammation is known to be contraceptive, impairing successful implantation of embryos (Kelly et al., 1969; Sheppard, 1987; Stanford and Mikolajczyk supra), the present inventor(s) postulated that a shorter period of exposure of the endometrium to copper ions and/or zinc ions, or at a lower dose, may produce a less intense inflammatory response that might possibly be capable of up-regulating the production of beneficial cytokines such as Vascular Endometrial Growth factor (VEGF) and Leukaemia inhibitory factor (LIF), but insufficient to cause harmful endometrial disruption that is normally observed in IUCD users.

The process of implantation of an embryo is a complex cascade of events requiring precise interaction between the action of ovarian steroids (e.g. estrogen and progesterone), and paracrine secretions from the embryo itself (e.g. hCG and cytokines) on the endometrium (Norwitz et al., 2001). Following ovulation and the subsequent rise in serum progesterone, endometrial glandular epithelial cells transform into highly active secretory cells that synthesise various substances (e.g. nutrients, growth factors and cytokines) that can enhance the development of the embryo and alter endometrial function. The uterine epithelium's production of LIF and VEGF are two key cytokines that play a critical role in aiding implantation (Norwitz et al., supra).

Evidence Supporting a Critical Role for LIF in Implantation

There is a considerable amount of evidence that points to a critical role for LIF in embryo implantation such as:

1. In the LIF "knock-out" mouse (i.e. a mouse model with no LIF production), normal embryos are created, yet they fail to implant into the uterus (Stewart et al., 1992; Chen et al., 2002). However, transfer of these LIF −/− embryos to wild type (LIF-producing) mice, or the artificial delivery of exogenous LIF to LIF −/− mice by injection on day 4 of pregnancy, restores normal implantation capacity (Stewart et al., supra; Chen et al., supra). Further, tissue-specific ablation of the LIF receptor in the murine uterine epithelium also results in implantation failure (Cheng et al., 2017). All these findings suggest that LIF activity is absolutely critical for implantation in mice.
2. The production of LIF by the endometrium peaks in the luteal phase of fertile women, at the precise time that the embryo normally initiates implantation (Charnock-Jones et al., 1994; Cullinan et al., 1996).
3. Endometrial LIF production is reduced in women with recurrent IVF implantation failure (Mikolajczyk et al., 2007; Choi et al., 2016), suggesting a critical role for LIF in the implantation process.
4. The addition of LIF to murine embryos in culture has been reported to enhance endometrial development to the "hatched" blastocyst stage, as well as increase trophoblast outgrowth in vitro (Lavranos et al., 1995). Similarly, exposure of murine embryos to LIF in vitro and their subsequent transfer using a trans-cervical technique similar to human IVF, has been reported to enhance implantation and pregnancy rates (Mitchell et al., 2002).
5. Conversely, blocking LIF action in vitro using either LIF neutralising antibodies (Mitchell et al., supra) or a polyethylene glycosylated LIF antagonist (Lalitkumar et al., 2013) has been reported to inhibit implantation potential in mice and humans respectively. Moreover, the delivery of LIF neutralising antibody to the uterine cavity on day 5 of pregnancy has been shown to significantly impair implantation in rhesus monkeys (Sengupta et al., 2006).
6. Poor endometrial development (thin endometrium), possibly mediated by insufficient vascular perfusion of the endometrium (Jinno et al., 2001), is a known cause for implantation failure. There is significant evidence that LIF is involved in angiogenesis in the endometrium and placenta (Alfer et al., 2017).

In summary, endometrial LIF production increases after ovulation and appears to assist implantation by enhancing embryo development, while also initiating events in the endometrium that appear to be critical for initial attachment and invasion of the embryo (i.e. implantation). Further, low endometrial LIF production is associated with reduced IVF success and infertility of unknown aetiology. Moreover, exposure to copper in the form of a copper-containing IUCD has previously been reported to decrease endometrial LIF expression and impair implantation (Güney et al., 2007). However, the impact of shorter periods of copper (or zinc) exposure on endometrial LIF production was hitherto unknown.

Evidence Supporting a Critical Role for VEGF in Implantation

There is also a considerable amount of evidence that points to a critical role for VEGF in embryo implantation, including:
1. The production of VEGF by the endometrium peaks in the mid-luteal phase of fertile women, at the precise time that the embryo normally initiates implantation. However, this mid-luteal peak in VEGF production is not seen in women with recurrent IVF implantation failure (Jee et al., 2009), suggesting a critical role for VEGF in the implantation process.
2. VEGF initiates endometrial tissue oedema by increasing vessel permeability and enhancing production of vasodilators (Rockwell et al., 2002). Oedema of the endometrial tissue (decidua) brings the uterine surface in close proximity to the blastocyst and appears to be important in establishing receptivity (apposition phase of implantation).
3. Gene polymorphisms that impair VEGF gene expression (e.g. the VEGF +405 CC polymorphism) have been found to be more common in women with recurrent IVF implantation failure (Boudjenah et al., 2012), while the VEGF +405 CC polymorphism is also associated with poorer implantation rates in "potentially fertile" women undergoing IVF for pure male factor infertility (Boudjenah et al., 2014).
4. Blocking VEGF activity by the administration of VEGF neutralising antibodies has been shown to prevent implantation in both primate and rodent models of pregnancy (Rockwell et al., supra; Ghosh and Sengupta, 2005).
5. The application of VEGF to embryos in culture has been shown to increase their speed of development/rate of cellular division (Hannan et al., 2011; Binder et al., 2014).
6. The in vitro exposure of human uterine epithelial cells to VEGF enhances their adhesiveness to common extracellular matrix (ECM) proteins found on the surface of the embryo (i.e. fibronectin and collagen), potentially assisting in the initial attachment of the embryo to the uterine epithelium (Binder et al., supra).
7. The glandular expression of VEGF in early luteal phase endometrial biopsies has been reported to be significantly higher in women who successfully conceived during IVF compared to those who did not conceive (Jinno et al., supra; Seo et al., 2011).
8. The level of VEGF in endometrial secretions obtained from uterine lavage (flushing uterine cavity with sterile saline in the mid-luteal phase) has been reported to be significantly lower in women experiencing recurrent IVF implantation failure than that seen in fertile controls (Hannan et al., supra), thereby suggesting VEGF may assist implantation.
9. The culture of mouse embryos in VEGF increased their adhesiveness to extracellular matrix (fibronectin)-coated plates in vitro, while also increasing the successful implantation of these VEGF-exposed embryos when transferred to pseudo-pregnant recipients (Binder et al., supra).
10. VEGF is known to play a critical role in the development of new capillaries (angiogenesis) and vascular perfusion of tissue, with thin endometrial development being linked to low capillary density and endometrial stromal VEGF expression (Miwa et al., 2009).

In summary, the available evidence suggests that endometrial-derived VEGF plays an important role in facilitating implantation by accelerating the development of the pre-implantation embryo, enhancing the adhesive interaction between the embryo and the uterine epithelium (improved binding to ECM proteins), while also increasing the underlying endometrial stroma oedema. A deficiency of VEGF action (e.g. through poor production by the epithelium or by the blocking of the action of VEGF) impedes implantation. As such, it has been considered that a therapy that could enhance endometrial production of VEGF may increase the rate of successful implantation of human embryos during IVF treatment. While copper has been previously reported to trigger an increase in endometrial VEGF production in IUCD users (Xin et al., 2004; Rafi et al., 2013), it was hitherto unknown whether a "short burst" exposure to copper ions, or the delivery of copper outside of the context of an IUCD "foreign body", would elicit a similar VEGF response, without causing endometrial disruption such as seen in IUCD users (Sadovsky et al., 1975; Stanford and Mikolajczyk, 2002). Similarly, prior to the experimentation described hereinafter, the impact of short term zinc exposure on endometrial VEGF production was unknown.

The present disclosure relates to the field of assisted reproductive technologies such as IVF and intra-uterine insemination (IUI) and, more particularly, relates to a method, formulation and device for enhancing implantation of transferred embryos to a subject. The methods (and formulation and device), involving the use of copper and optionally zinc ions, potentially offers a simple and relatively inexpensive treatment to enhance embryo implantation, particularly in women who have experienced recurrent implantation failure (RIF) following IVF or other assisted reproductive technology treatments.

SUMMARY

In a first aspect, the present disclosure provides a method of enhancing embryo implantation in a subject (i.e. a woman or other female animal), wherein the method comprises administering to the uterine cavity of the subject a formulation comprising copper and/or zinc in an amount effective to stimulate endometrial production of leukaemia inhibitory factor (LIF) and/or vascular endothelial growth factor (VEGF).

In a second aspect, the present disclosure provides a method of enhancing embryo implantation in a subject, wherein the method comprises inserting into the uterine cavity of the subject a device comprising copper and/or zinc for a period of time that is effective to stimulate endometrial production of leukaemia inhibitory factor (LIF) and/or vascular endothelial growth factor (VEGF).

The methods are particularly suitable for use with women undergoing treatment by any of the assisted reproductive technologies, and particularly those involving the transfer of embryos such as in vitro fertilisation (IVF) and variants including IVF-ICSI (intracytoplasmic sperm injection).

In a third aspect, the present disclosure provides a formulation for enhancing embryo implantation in a subject, said formulation being suitable for administration to the uterine cavity and comprising copper and/or zinc in an amount effective to stimulate endometrial production of leukaemia inhibitory factor (LIF) and/or vascular endothelial growth factor (VEGF), and wherein said formulation optionally comprises one or more pharmaceutically acceptable carrier and/or excipient.

In some preferred embodiments, the copper and/or zinc is provided in a solution form, such as a solution comprising copper chloride ($CuCl_2$) and/or zinc chloride ($ZnCl_2$).

DETAILED DESCRIPTION

Figure 1A:
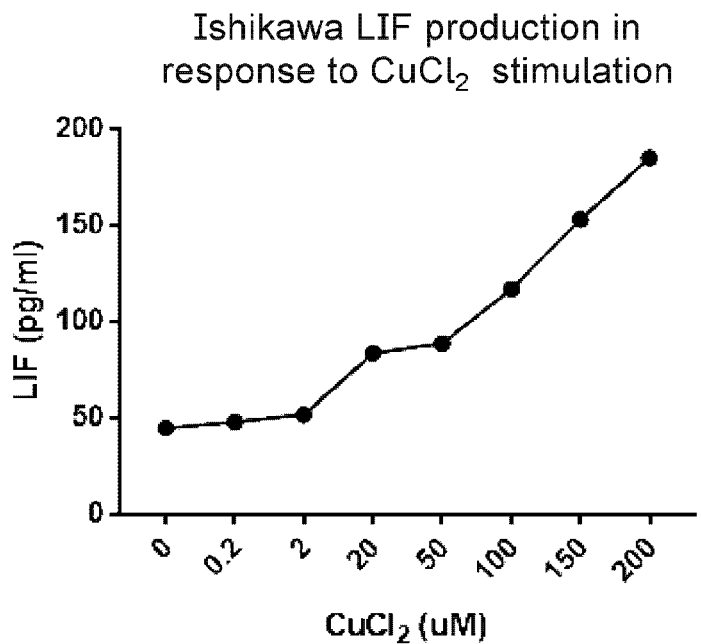
FIG. 1 provides graphical results showing the effect of metal ions provided by $CuCl_2$ (A) and $ZnCl_2$ (B) solutions on the production of LIF from cultures of the human Ishikawa endometrial adenocarcinoma cell line (Ishikawa cells)

In experimentation described hereinafter, the present inventor(s) found that human endometrial cells subjected to a short term exposure of copper ions ($Cu^{2+}$) and/or zinc ions ($Zn^{2+}$), as provided by salt solutions or solid metal wire or sheets ("metal implants"), produced increased amounts of leukaemia inhibitory factor (LIF) and vascular endothelial growth factor (VEGF), both of which are believed to have an important role in embryo implantation. Moreover, when day 3 embryos were grown in "conditioned" media including the metal ions, significant increases in the surface area of trophoblast outgrowth resulted, thereby indicating improved embryo health and implantation potential. The present disclosure is therefore directed to novel methods (and a formulation and device), involving the use of copper and optionally zinc ions to enhance endometrial production of LIF and/or VEGF, to enhance embryo implantation in women (and other female animals) including women who have experienced recurrent implantation failure (RIF) following IVF or other assisted reproductive technology treatments.

In a first aspect, the present disclosure provides a method of enhancing embryo implantation in a subject (i.e. a woman or other female animal), wherein the method comprises administering to the uterine cavity of the subject a formulation comprising copper and/or zinc in an amount effective to stimulate endometrial production of leukaemia inhibitory factor (LIF) and/or vascular endothelial growth factor (VEGF).

The method is suitable for use with women undergoing treatment by any of the assisted reproductive technologies, such as those involving the transfer of embryos such as in vitro fertilisation (IVF) and variants including IVF-ICSI (intracytoplasmic sperm injection) and in vitro maturation (IVM) treatments, as well as intrauterine-insemination (IUI) therapy. However, the method is also applicable for women wanting to improve their prospects of pregnancy through natural conception.

The method may be particularly suitable for use with women who show inadequate or "thin" endometrial development (e.g. an endometrial thickness of 7 mm or less), which is a recognised cause of infertility and implantation failure following embryo transfer (Kasius et al., 2014; Yuan et al., 2016). In this regard, it is considered that by stimulating endometrial production of LIF and/or VEGF, which are both believed to stimulate endometrial angiogenesis, the method may be performed so as to improve angiogenesis and thereby treat thin endometrium-related implantation failure. Accordingly, the present disclosure also extends to a method of treating women experiencing inadequate endometrial development. Women experiencing inadequate endometrial development may be readily identified by standard ultrasound imaging (e.g. transvaginal ultrasound).

Further, while the emphasis of the present disclosure resides with women, those skilled in the art will recognise that the methods (and formulation and device) disclosed herein are also applicable to other non-human female subjects (i.e. other female animals) such as, for example, livestock (e.g. cattle, horses and sheep), exotic animals (e.g. pandas, big cats such as tigers and lions, elephants and the like) and companion animals (such as dogs and cats), particularly where assisted reproductive technologies (especially those involving the transfer of embryos) are being employed to assist in achieving pregnancy.

In some embodiments, the formulation used in the method of the first aspect comprises copper and, optionally, zinc.

In other embodiments, the formulation comprises copper or copper and zinc.

In yet other embodiments, the formulation comprises zinc.

The copper and/or zinc may each be present in the formulation in, for example, one or more of an elemental (e.g. pure), alloy, complexed, oxidised, salt (including esterified salts and other salts formed from organic acids) or solution forms. Preferably, the copper and/or zinc is present in such a form that may provide a source of copper/zinc ions within the uterus. Such a form may include nanoparticle forms. The formulation may be in the form of, for example, a liquid, semi-solid or solid dosage form.

In some embodiments, the copper and/or zinc is provided in a solution form, such as a solution comprising copper chloride ($CuCl_2$) and/or zinc chloride ($ZnCl_2$), a solution comprising copper sulphate ($CuSO_4$) and/or zinc sulphate ($ZnSO_4$), copper gluconate and/or zinc gluconate, a solution of copper chlorate ($Cu(ClO_4)_2$) and/or zinc chlorate ($Zn(ClO_3)_2$), a solution comprising copper nitrate ($Cu(NO_3)_2$) and/or zinc nitrate ($Zn(NO_3)_2$) or a solution comprising copper bromide (CuBr) and/or zinc bromide ($ZnBr_2$) or mixtures thereof (e.g. a solution of $CuCl_2$ and copper gluconate, or a solution of $CuCl_2$ and $ZnSO_4$). Such solutions may provide a source of copper/zinc ions within the uterus.

In other embodiments, the copper and/or zinc is provided in a semi-solid (e.g. gel or foam) form. For example, a gel comprising $CuCl_2$ and/or $ZnCl_2$ or a gel comprising nanoparticles of copper and/or zinc or which comprise $CuCl_2$ and/or $ZnCl_2$. The gel may, for example, provide a short term depot dosage form within the uterus. As will be appreciated by those skilled in the art, biodegradable gel depots may also be formed in situ using well known injectable in situ depot-forming drug delivery systems. Such a gel may provide a source of copper/zinc ions within the uterus, which may enable a controlled and/or sustained release of copper/zinc ions. In some particular embodiments of suitable gel formulations, the copper and/or zinc may be formulated with hydroxyethyl cellulose and glycerol, and in one example, the copper and/or zinc may be formulated with ExEm-gel® (IQ Medical Ventures BV; Rotterdam, The Netherlands).

In yet other embodiments, the copper and/or zinc is provided in a solid dosage form. For instance, the copper and/or zinc may be provided as small, dissolvable crystals or other particles (e.g. a powder or nanoparticles of metal). For example, crystals or other particles of $CuCl_2$ and/or $ZnCl_2$. Such crystals or particles may be administered in a suitable carrier liquid or gel (e.g. which may be prepared shortly before administration) or as provided in a dissolvable tablet or capsule administered by a suitable uterine applicator device. Such crystals or other particles may provide a source of copper/zinc ions within the uterus.

It is to be appreciated that the formulation is something other than an IUCD.

Also, it is to be appreciated that, preferably, the formulation used in the method of the first aspect is not provided as any solid form or within any device that requires surgical removal from the uterus after treatment. In this regard, the dosage forms of the embodiments described above will, in many if not all cases, enable a relatively non-invasive and "comfortable" treatment by allowing administration by simple means (e.g. by the use of a device such as, for example, a flexible catheter "loaded" with the formulation and passed through the cervical canal and into the uterine cavity) without any need for subsequent removal of the formulation.

The formulation may comprise one or more pharmaceutically acceptable carrier and/or excipient, which may vary depending upon the dosage form to be adopted. For example, for a solution of a salt of copper and/or zinc, the formulation may comprise water or normal (isotonic) saline. For a gel comprising a salt of copper and/or zinc, the formulation may comprise a biocompatible and biodegradable polymer excipient (e.g. lactide/glycolide polymers, and hydroxyethyl cellulose etc); in such gels, the copper and/or zinc may be present as esterified salt(s), particularly one comprising a saturated fatty acid such as decanoic (capric) acid (e.g. copper ($2^+$) decanoate), or salt(s) of other organic acids such as salts of D-gluconic acid (e.g. copper gluconate). As would be appreciated by those skilled in the art, the formulation may further comprise one or more substance selected from preservatives (e.g. sodium benzoate, sorbic acid and esters of p-hydroxybenzoic acid), binders (e.g. starch, gelatin, natural sugars such as glucose and anhydrous lactose, and natural and synthetic gums such as acacia, hydroxyethyl cellulose, carboxymethyl cellulose and polyethylene glycol), lubricants (e.g. sodium oleate, sodium stearate, magnesium stearate and the like), humectants (e.g. glycerol), anti-oxidants, suspending agents, stabilising agents, coating agents and solubilising agents, as may be required and/or desirable for a particular dosage form.

Further, the formulation may comprise one or more other substance which stimulate the production or activity of LIF, VEGF or other cytokines, growth factors etc that may be beneficial to embryo implantation (e.g. integrins). For example, the formulation may further comprise an effective amount of benzoic acid which is believed to cause an increase in the expression of LIF and the integrins, V3 and V5, to promote embryo implantation (Korean Patent Publication No 20160108690; the entire content of which is to be regarded as incorporated herein by reference).

The formulation is administered to the subject in an amount effective to stimulate endometrial production of leukaemia inhibitory factor (LIF) and/or vascular endothelial growth factor (VEGF).

In some embodiments, that amount will typically be one that provides copper ions to the uterine fluid in an amount that is at least 500 ppb and/or provides zinc ions to the uterine fluid in an amount that is at least 50 ppb. However, preferably, the formulation is administered to the subject in an amount that provides copper ions to the uterine fluid in an amount that is at least 1250 ppb (more, preferably, at least 2500 ppb) and/or provides zinc ions to the uterine fluid in an amount that is at least 100 ppb (more, preferably, at least 250 ppb). As will be readily appreciated by those skilled in the art, a sample of uterine fluid may be obtained by aspiration using an embryo transfer catheter (Ametzazurra et al., 2009) and assessed for metal ion content using mass spectroscopy. However, suitable amounts of the formulation (i.e. to provide copper ions to the uterine fluid in an amount that is at least 500 ppb and/or provide zinc ions to the uterine fluid in an amount that is at least 50 ppb) may otherwise be tested for by adding varying amounts of the formulation to a "model" uterine fluid and amount (e.g. a volume of 5 ml of a suitable culture medium such as αMEM or G2 media or a suitable embryo transfer medium) at 37° C. and assessing the metal ion content by mass spectroscopy in a sample of the media taken at a suitable time point(s) (e.g. 2 minutes and/or 5 minutes after addition of the formulation). It is considered that the "release" of copper and/or zinc ions into the media will be substantially comparable to that which will occur in the uterus. Accordingly, detection of an amount of copper ions in the tested sample of at least 500 ppb may indicate an amount of the formulation (comprising copper) suitable for administration. Similarly, the detection of an amount of zinc ions in the tested sample of at least 50 ppb indicates an amount of the formulation (comprising zinc) suitable for administration.

In some embodiments, the amount of the formulation that is effective to stimulate endometrial production of leukaemia inhibitory factor (LIF) and/or vascular endothelial growth factor (VEGF) may be an amount that provides copper to the endometrial fluid in an amount in the range of about 0.025 µg to about 12.5 µg (preferably about 0.25 µg to about 10 µg, more preferably about 0.5 µg to about 5 µg, and most preferably about 0.05 µg to about 2.5 µg) and/or zinc in an amount in an equivalent range of about 0.05 µg to about 12.5 µg (preferably about 0.25 µg to about 10 µg, more preferably about 0.5 µg to about 5 µg, and most preferably about 0.05 µg to about 2.5 µg).

In some embodiments of a formulation comprising a solution of $CuCl_2$, the formulation comprises a concentration of $CuCl_2$ of at least about 20 µM, preferably at least about 50 µM. In particular, the formulation preferably comprises a solution of $CuCl_2$ at a concentration in the range of about 20 µM to about 200 µM, more preferably in the range of 50 µM to 150 µM. Such a formulation may be administered to the subject in a volume of about 100 to 1000 µl, more preferably about 150 to 500 µl.

In some embodiments of a formulation comprising a solution of $ZnCl_2$, the formulation comprises a concentration of $ZnCl_2$ of at least about 20 µM, preferably at least about 50 µM. In particular, the formulation preferably comprises a solution of $ZnCl_2$ at a concentration in the range of about 20 µM to about 150 µM, more preferably in the range of 50 µM to 125 µM. Such a formulation may be administered to the subject in a volume of about 100 to 1000 µl, more preferably about 150 to 500 µl.

Where the subject is undergoing treatment by any of the assisted reproductive technologies involving the transfer of embryos, the formulation is preferably administered to the subject prior to embryo transfer and within the same menstrual cycle (which in the context of IVF, would be considered as the same IVF cycle). Preferably, the formulation is administered to the subject at a time prior to embryo transfer that is sufficient to stimulate a level of endometrial production of LIF and/or VEGF to enhance embryo implantation. Preferably, the subject is given a single administration of the formulation prior to embryo transfer. In some embodiments, the formulation is administered to the subject no more than 14 days prior to the embryo transfer, preferably, no more than about 10 days prior to the embryo transfer and, more preferably, no more than about 5 days prior to the embryo transfer. In some embodiments, the formulation is administered 5 days prior to the embryo transfer, or 4 days prior to the embryo transfer, or 3 days prior to the embryo transfer, or 2 days prior to the embryo transfer, or 1 day prior to the embryo transfer. In other embodiments, the formulation is administered on the same day as the embryo transfer; for example, shortly before the embryo transfer (e.g. within 3 hours, or 60 minutes, or 30 minutes, or 10 minutes, or 5 minutes, or 1 minute of the embryo transfer) or, less preferably, immediately after the embryo transfer (e.g. within 10 minutes of the embryo transfer). It may also be an option to administer the formulation concurrently with the embryo transfer. For instance, the embryo may be transferred to the subject in the formulation which might, in such embodiments, further comprise components and substances typically included in standard embryo transfer media (e.g. as found in EmbryoGlue™ embryo transfer media; Vitrolife, Gothenburg, Sweden). Alternatively, the formulation may be provided for concurrent administration with the embryo transfer by coating or impregnating the embryo transfer catheter (or at least a portion of a distal section of an embryo transfer catheter that is inserted into the uterine cavity, or a part thereof) in the formulation; in such an embodiment, it may be preferred if a part of the distal section of the catheter that is a short distance away (eg 1-3 cm) from the tip of the catheter (from where the embryo is ejected) is coated or impregnated in the formulation.

Notwithstanding what is described in the preceding paragraph, in some preferred embodiments of the method of the first aspect, there is no administration of formulation either at the time of embryo transfer (ie concurrently) or after the embryo transfer. That is, the method of such embodiments comprises administering the formulation only prior to embryo transfer, preferably as a single administration.

For women experiencing inadequate endometrial development, the formulation will be administered to the uterine cavity at least once in the relevant menstrual cycle, and preferably during the time between the cessation of the menses and ovulation or commencement of the increase in progesterone that accompanies ovulation. In some embodiments, the formulation may be administered on multiple occasions during this period (eg one administration per day over a series of days).

Where the subject is undergoing treatment by IUI, the formulation is preferably administered to the subject prior to IUI and within the same menstrual cycle (i.e. within the same menstrual cycle as the insemination is being performed). Preferably, the formulation is administered to the subject at a time prior to ovulation/insemination that is sufficient to stimulate a level of endometrial production of LIF and/or VEGF to enhance embryo implantation. Preferably, the subject is given a single administration of the formulation prior to insemination. In some embodiments, the formulation is administered to the subject no more than 9 days prior to ovulation and, preferably, no more than about 5 days prior to ovulation. In some embodiments, the formulation is administered 5 days prior to ovulation, or 4 days prior to the ovulation, or 3 days prior to ovulation, or 2 days prior to ovulation, or 1 day prior to ovulation. In other embodiments, the formulation is administered on the same day as ovulation. Preferably, there is no administration of formulation either at the time of insemination (ie concurrently) or after the insemination. However, for women experiencing inadequate endometrial development, the formulation will be administered to the uterine cavity at least once in the relevant menstrual cycle; preferably during the time between the cessation of the menses and ovulation or commencement of the increase in progesterone that accompanies ovulation (e.g. the formulation may be administered on multiple occasions during this period (e.g. one administration per day over a series of days)).

Where the subject is hoping to achieve pregnancy through natural conception, the formulation is preferably administered to the subject prior to ovulation and within the same menstrual cycle. Preferably, the formulation is administered to the subject at a time prior to ovulation that is sufficient to stimulate a level of endometrial production of LIF and/or VEGF to enhance embryo implantation. In some embodiments, the formulation is administered to the subject no more than 9 days prior to ovulation and, preferably, no more than about 5 days prior to ovulation. In some embodiments, the formulation is administered 5 days prior to ovulation, or 4 days prior to ovulation, or 3 days prior to ovulation, or 2 days prior to ovulation, or 1 day prior to ovulation. In other embodiments, the formulation is administered on the same day as ovulation. For women experiencing inadequate endometrial development, the formulation will be administered to the uterine cavity at least once in the relevant menstrual cycle; preferably during the time between the cessation of the menses and ovulation or commencement of the increase in progesterone that accompanies ovulation (e.g. the formulation may be administered on multiple occasions during this period (e.g. one administration per day over a series of days)).

In a second aspect, the present disclosure provides a method of enhancing embryo implantation in a subject (i.e. a woman or other female animal), wherein the method comprises inserting into the uterine cavity of the subject a device comprising copper and/or zinc for a period of time that is effective to stimulate endometrial production of leukaemia inhibitory factor (LIF) and/or vascular endothelial growth factor (VEGF).

A device (or "uterine device") suitable for use in the method of the second aspect will typically be of an elongated form (e.g. akin to a surgical probe or an embryo transfer catheter). As such, the device may comprise a distal section and a proximal base section, and the step of inserting the device into the uterine cavity involves inserting at least a portion of the distal section into the uterine cavity. The proximal base section, which remains exterior to the subject while the distal section is inserted in the uterine cavity, enables the insertion and retraction of the device. The portion of the distal section that is inserted into the uterine cavity, or a part thereof, may comprise or be provided with copper and/or zinc and may elicit copper and/or zinc ions to stimulate endometrial production of LIF and/or VEGF, while the remainder of the device may comprise stainless steel or a biocompatible polymer. In some embodiments, the portion of the distal section that is inserted into the uterine cavity, or a part thereof, may comprise or be coated with copper and/or zinc metal which may elicit copper and/or zinc ions by corrosion (i.e. the copper and/or zinc is provided as elemental metal, which may have, on its surface an oxidised form of the metal and elicits metal ions by corrosion caused when the device is brought into contact with uterine fluid following insertion of the device into the uterine cavity). In other embodiments, the copper and/or zinc metal may be provided in the form of nanoparticles, to increase the surface area available for corrosion, effectively accelerating the rate of delivery of the metal ions to the uterine fluid. In a particular embodiment, the device may be an embryo transfer catheter (e.g. a catheter of the kind used for the transfer of embryos (suspended in small volumes of transfer media) to women undergoing IVF treatment) wherein the distal section that is inserted into the uterine cavity, or a part thereof, comprises or is provided with copper and/or zinc. Where the device is to be used with a subject undergoing treatment by any of the assisted reproductive technologies involving the transfer of embryos, this embodiment enables, if desired, the delivery of the metal ions to the uterine fluid at the time of the embryo transfer. Moreover, the use of a device as described, may avoid any potential disadvantage associated with the administration of a liquid formulation (e.g. a solution of $CuCl_2$ and/or $ZnCl_2$), by enabling the delivery of the copper and/or zinc ions without adding to the uterine cavity fluid volume. This may be a significant advantage in embodiments where the delivery of the metal ions is to be performed at the time of embryo transfer, as the application of excess embryo transfer media during the embryo transfer process has been linked with a reduction in IVF success rates (Sigalos et al., 2017).

The device is inserted into the uterine cavity for a period of time effective to stimulate endometrial production of leukaemia inhibitory factor (LIF) and/or vascular endothelial growth factor (VEGF). Those skilled in the art will recognise that this period of time will be short (i.e. to avoid the inhibitory effect of long term uterine exposure to copper and/or zinc ions on embryo implantation as achieved with exposure to an IUCD). Typically, the period will be one that provides copper ions to the uterine fluid in an amount that is at least 500 ppb (preferably, at least 1250 ppb, and more preferably, at least 2500 ppb) and/or provides zinc ions to the uterine fluid in an amount that is at least 50 ppb (more preferably, at least 250 ppb). In any case, this period will be rarely, if ever, longer than 60 minutes and, typically, will be no more than about 10 minutes. More preferably, the period will be about 1 minute, or about 2 minutes, or about 3 minutes, or about 4 minutes or about 5 minutes. However, it will be understood that the rate of release of the copper and/or zinc ions into the uterine fluid may be varied (which, in turn, may require the insertion period to be increased or reduced). For example, the contact of copper and/or zinc metal with uterine fluid will cause it to corrode, releasing the metal ions into solution. By placing other metals in contact with the copper and/or zinc metal, the release of the copper and/or zinc ions may be slowed or accelerated depending on the relative positions of the metals on the galvanic series (Zipper et al., 1977).

Where the subject is undergoing treatment by any of the assisted reproductive technologies involving the transfer of embryos, the device is preferably inserted into the uterine cavity of the subject prior to embryo transfer and within the same menstrual cycle (which in the context of IVF, would be considered as the same IVF cycle). Preferably, the device is inserted at a time prior to embryo transfer that is sufficient to stimulate a level of endometrial production of LIF and/or VEGF to enhance embryo implantation. Preferably, the device is inserted into the uterine cavity of the subject on a single occasion prior to embryo transfer. In some embodiments, the device is inserted no more than 14 days prior to the embryo transfer, preferably no more than about 10 days prior to the embryo transfer and, more preferably, no more than about 5 days prior to the embryo transfer. In some embodiments, the device is inserted 5 days prior to the embryo transfer, or 4 days prior to the embryo transfer, or 3 days prior to the embryo transfer, or 2 days prior to the embryo transfer, or 1 day prior to the embryo transfer. In other embodiments, the device is inserted on the same day as the embryo transfer; for example, shortly before the embryo transfer (e.g. within 3 hours, or 60 minutes, or 30 minutes, or 10 minutes, or 5 minutes, or 1 minute of the embryo transfer) or, less preferably, immediately after the embryo transfer (e.g. within 10 minutes of the embryo transfer). Further, as mentioned above, where the device is an embryo transfer catheter, the delivery of the copper and/or zinc ions to the uterine fluid can be achieved at the time of the embryo transfer.

In a third aspect, the present disclosure provides a formulation for enhancing embryo implantation in a subject, said formulation being suitable for administration to the uterine cavity and comprising copper and/or zinc in an amount effective to stimulate endometrial production of leukaemia inhibitory factor (LIF) and/or vascular endothelial growth factor (VEGF), and wherein said formulation optionally comprises one or more pharmaceutically acceptable carrier and/or excipient.

In some embodiments, the formulation comprises copper and, optionally, zinc. In other embodiments, the formulation comprises copper or copper and zinc. In yet other embodiments, the formulation comprises zinc.

The copper and/or zinc may each be present in the formulation in, for example, one or more of an elemental (e.g. pure), alloy, complexed, oxidised, salt (including esterified salts and other salts formed from organic acids) or solution forms. Preferably, the copper and/or zinc is present in such a form that may provide a source of copper/zinc ions within the uterus. The formulation may be in the form of, for example, a liquid, semi-solid or solid dosage form.

In some preferred embodiments, the copper and/or zinc is provided in a solution form, such as a solution comprising copper chloride ($CuCl_2$) and/or zinc chloride ($ZnCl_2$). Such a solution may provide a source of copper/zinc ions within the uterus. Preferably, the solution is an isotonic saline solution of $CuCl_2$ and/or $ZnCl_2$.

In other embodiments, the copper and/or zinc is provided in a semi-solid (e.g. gel or foam) form. For example, a gel comprising $CuCl_2$ and/or $ZnCl_2$ or a gel comprising nanoparticles of copper and/or zinc or which comprise $CuCl_2$ and/or $ZnCl_2$. The gel may, for example, provide a short term depot dosage form within the uterus providing a source of copper/zinc ions within the uterus, which may enable a controlled and/or sustained release of copper/zinc ions (e.g. a gel wherein the copper and/or zinc is formulated with hydroxyethyl cellulose and glycerol).

In yet other embodiments, the copper and/or zinc is provided in a solid dosage form such as small, dissolvable crystals or other particles (e.g. a powder or metal nanoparticles) of, for example, crystals or other particles of $CuCl_2$ and/or $ZnCl_2$, which may be administered in a suitable carrier liquid or gel (e.g. which may be prepared shortly before administration) or as provided in a dissolvable tablet or capsule. Such crystals or other particles may provide a source of copper/zinc ions within the uterus.

The formulation may comprise one or more pharmaceutically acceptable carrier and/or excipient such as those described above. Also, the formulation may further comprise one or more substance selected from preservatives, binders, lubricants, anti-oxidants, suspending agents, stabilising agents, coating agents and solubilising agents, such as those described above. In addition, the formulation may comprise one or more other substances which stimulate the production or activity of LIF, VEGF or other cytokines, growth factors etc that may be beneficial to embryo implantation (e.g. integrins). The formulation may also comprise components and substances typically included in standard embryo transfer media.

In some preferred embodiments, the formulation comprises a solution of $CuCl_2$ comprising a concentration of $CuCl_2$ of at least about 20 µM, preferably at least about 50 µM. In particular, the formulation preferably comprises a solution of $CuCl_2$ at a concentration in the range of about 20 µM to about 200 µM, more preferably in the range of 50 µM to 150 µM. In some other preferred embodiments, the formulation comprises a solution of $ZnCl_2$ comprising a concentration of $ZnCl_2$ of at least about 20 µM, preferably at least about 50 µM. In particular, the formulation preferably comprises a solution of $ZnCl_2$ at a concentration in the range of about 20 µM to about 150 µM, more preferably in the range of 50 µM to 125 µM.

Where the formulation is provided as a liquid (e.g. a formulation comprising a solution of $CuCl_2$ and/or $ZnCl_2$), the formulation may be provided in a package or device adapted for administration of the formulation to the uterine cavity; for example, a flexible catheter "loaded" with the formulation which is adapted to be passed through the cervical canal and into the uterine cavity. Such a catheter may be akin to those used for the transfer of embryos (suspended in small volumes of transfer media) to women undergoing IVF treatment. The catheter may comprise a biocompatible polymer and be hermetically sealed for transport and storage containing the liquid formulation, which may be provided in a reservoir or bulb located at or adjacent to the tip of the catheter. The tip of the catheter may comprise a frangible section which may be broken just prior to use. Otherwise, the tip may be sealed with a readily removable cap or lid. The amount of the formulation contained within the catheter may be as little as 100 to 1000 µl or, more preferably, a volume in the range of about 150 to 500 µl.

In a fourth aspect, the present disclosure provides the use of a formulation of copper and/or zinc for enhancing embryo implantation in a subject, wherein the formulation is adapted to be administered to the uterine cavity of the subject in an amount effective to stimulate endometrial production of leukaemia inhibitory factor (LIF) and/or vascular endothelial growth factor (VEGF).

In a fifth aspect, the present disclosure provides the use of copper and/or zinc in the manufacture of a formulation for enhancing embryo implantation in a subject, wherein the formulation is adapted to be administered to the uterine cavity of the subject in an amount effective to stimulate endometrial production of leukaemia inhibitory factor (LIF) and/or vascular endothelial growth factor (VEGF).

In the uses of the fourth and fifth aspects, the subject may be a woman undergoing treatment by any of the assisted reproductive technologies, particularly those involving the transfer of embryos such as in vitro fertilisation (IVF) and variants including IVF-ICSI (intracytoplasmic sperm injection) and in vitro maturation (IVM) treatments. However, the subject may also be a woman receiving intrauterine-insemination (IUI) therapy, or a woman wanting to improve their prospects of pregnancy through natural conception. The subject may also be selected from other non-human female subjects such as, for example, livestock.

The copper and/or zinc may each be present in the formulation in, for example, one or more of an elemental (e.g. pure), alloy, complexed, oxidised, salt (including esterified salts and other salts formed from organic acids) or solution forms. Preferably, the copper and/or zinc is present in such a form that may provide a source of copper/zinc ions within the uterus. The formulation may be in the form of, for example, a liquid, semi-solid or solid dosage form. In some embodiments, the copper and/or zinc is provided in a solution form, such as a solution comprising copper chloride ($CuCl_2$) and/or zinc chloride ($ZnCl_2$). Such a solution may provide a source of copper/zinc ions within the uterus.

The formulation may comprise one or more pharmaceutically acceptable carrier and/or excipient such as those described above. Also, the formulation may further comprise one or more substance selected from preservatives, binders, lubricants, anti-oxidants, suspending agents, stabilising agents, coating agents and solubilising agents, such as those described above. In addition, the formulation may comprise one or more other substance which stimulate the production or activity of LIF, VEGF or other cytokines, growth factors etc that may be beneficial to embryo implantation (e.g. integrins).

In some preferred embodiments, the formulation comprises a solution of $CuCl_2$ comprising a concentration of $CuCl_2$ of at least about 20 μM, preferably at least about 50 μM. In particular, the formulation preferably comprises a solution of $CuCl_2$ at a concentration in the range of about 20 μM to about 200 μM, more preferably in the range of 50 μM to 150 μM. In some other preferred embodiments, the formulation comprises a solution of $ZnCl_2$ comprising a concentration of $ZnCl_2$ of at least about 20 μM, preferably at least about 50 μM. In particular, the formulation preferably comprises a solution of $ZnCl_2$ at a concentration in the range of about 20 μM to about 150 μM, more preferably in the range of 50 μM to 125 μM.

The method and formulation of the present disclosure is hereinafter further described by way of the following, non-limiting examples and accompanying figures.

EXAMPLES

Example 1

Effect of Metal Ions on In Vitro LIF and VEGF Production

Materials and Methods

The human Ishikawa endometrial adenocarcinoma cell line (Sigma-Aldrich; St Louis, MO, United States of America) was used to model the endometrium's response to copper and zinc metal ions ($Cu^{2+}$ and $Zn^{2+}$). Cells were grown in T75 flasks (Nalge Nunc International, Rochester, NY, United States of America) in Ishikawa medium, consisting of αMEM (Sigma-Aldrich) supplemented with 5% foetal bovine serum (Invitrogen Corp, Carlsbad, CA, United States of America), 2 mM glutamine (Sigma-Aldrich) and 1% non-essential amino acids (Sigma-Aldrich) without antibiotics at 37° C. under a gas atmosphere of 5% $CO_2$ in air. Medium was refreshed every 48 hours. Cells were subcultured using 0.25% trypsin/EDTA (Invitrogen). For metal ion exposure experiments, cells were seeded onto 2-well chamber slides (Ibidi, Martinsried, Germany). After the endometrial cells had attached and reached 80-90% confluence they were then exposed to copper and zinc metal ions using two approaches (salt solution or metal implant) as described below.

Metal Ions in Solution

Copper or zinc chloride (Sigma-Aldrich) was dissolved in Ishikawa medium to produce salt solutions at various concentrations in the range of 0.2 μM and 200 μM, before being applied to Ishikawa cells seeded into 2-well chamber slides for a period of 8 hours. Following the 8 hours exposure, culture media were removed, centrifuged at 1000 g for 10 minutes at 4° C. to pellet any cellular debris, and then the supernatants were stored in Eppendorf tubes at −80° C. Subsequently, the supernatants were assayed for both LIF and VEGF content using a multiplex immunoassay system (elisakit.com, Scoresby, VIC, Australia).

Metal Implants

Implants composed of various metals were generated using either metal wire (copper) or metal sheets of various types (copper, zinc, aluminium and gold). In some cases, the implants comprised sheets of two metals (bimetal implants), particularly copper and zinc (CuZn), zinc and aluminium (ZnAl) and zinc and gold (ZnAu). Following heat sterilisation, the implants were placed in direct contact with Ishikawa cells and then seeded onto 2-well chamber slides in Ishikawa medium or G2 embryo culture medium (Vitrolife) using sterilised surgical tweezers for a period of between 1 and 5 minutes, before being removed. The Ishikawa cell supernatants were collected 4-8 hours later, centrifuged at 1000 g at 4° C. for 10 minutes, and then frozen at −80° C. for later metal ion and cytokine assessment by mass spectroscopy.

Results

Figure 1B:
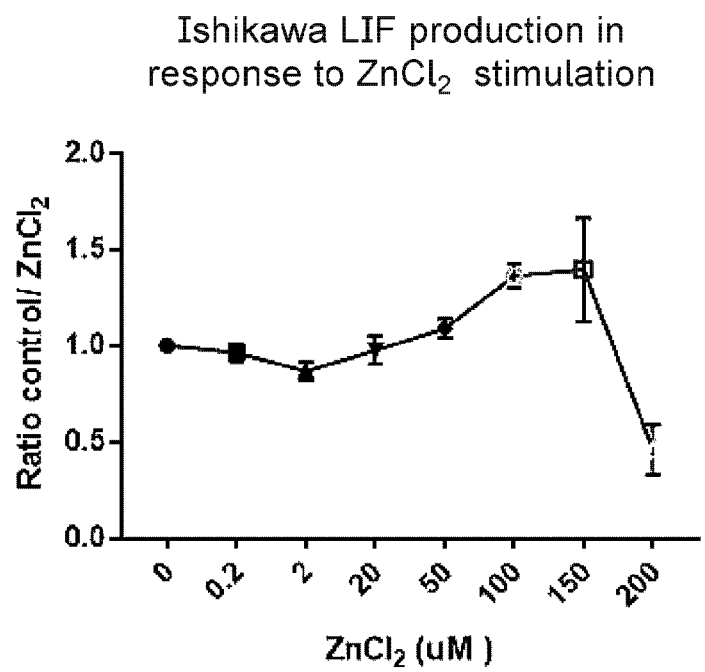
Figure 2A:
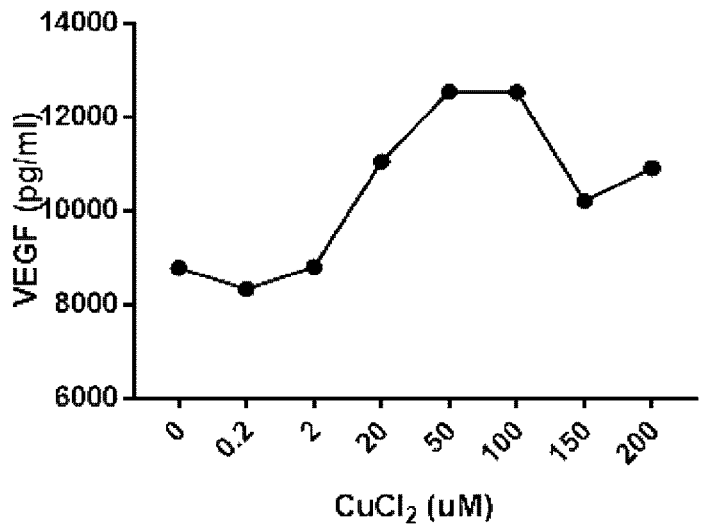
FIG. 2 provides graphical results showing the effect of metal ions provided by $CuCl_2$ (A) and $ZnCl_2$ (B) solutions on the production of VEGF from cultures of Ishikawa cells.
Figure 2B:
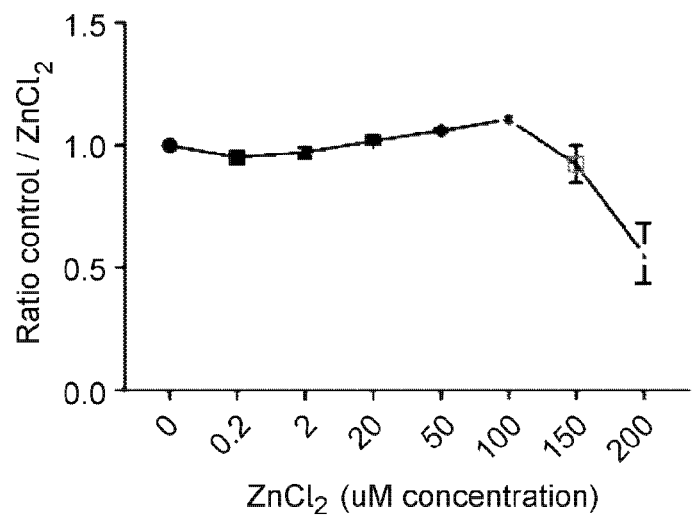

With the solutions of metal ions, it was found that copper ions produced a significant increase in LIF production above baseline at a $CuCl_2$ concentration exceeding 2 μM (see FIG. 1A), with LIF production increasing 420% above baseline at a concentration of 200 μM. No toxicity in relation to LIF production was observed in the tested dose range within the 8 hour incubation time frame. The zinc ions also produced a significant increase in LIF production compared to controls at $ZnCl_2$ concentrations ranging from 50 μM to 150 μM (see FIG. 1B). However, when administered at doses exceeding 150 µM, the zinc ions appeared to cause toxicity, with a reduction in LIF production being observed (FIG. 2A). In relation to VEGF production, the copper chloride solutions produced a significant increase in VEGF production at concentrations above 20 µM, peaking at 100 µM $CuCl_2$ concentration. On the other hand, zinc chloride produced no significant increase in VEGF compared to controls, but did appear to reduce VEGF production from a concentration of 150 µM (FIG. 2B).

Figure 3A:
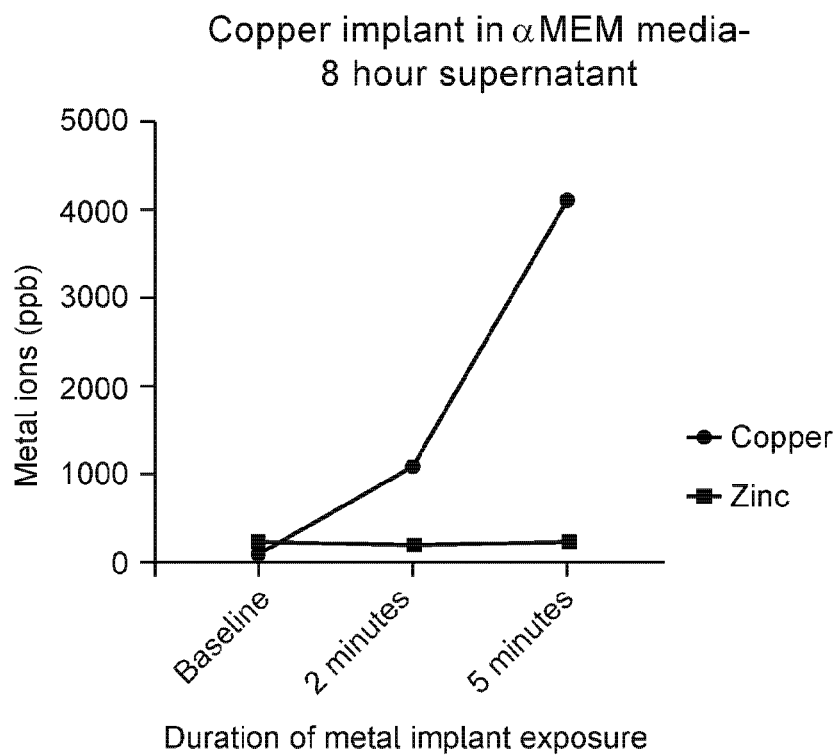
FIG. 3 shows the results of experimentation conducted to assess the amount of copper and zinc ions released from metal implants into cultures of Ishikawa cells in αMEM or G2 culture media. The metal implants, (A) copper sheet implant (Cu) and (B) copper-zinc sheet bimetal implant (CuZn), were placed into the cell cultures for durations of 2 minutes and 5 minutes.
Figure 3B:
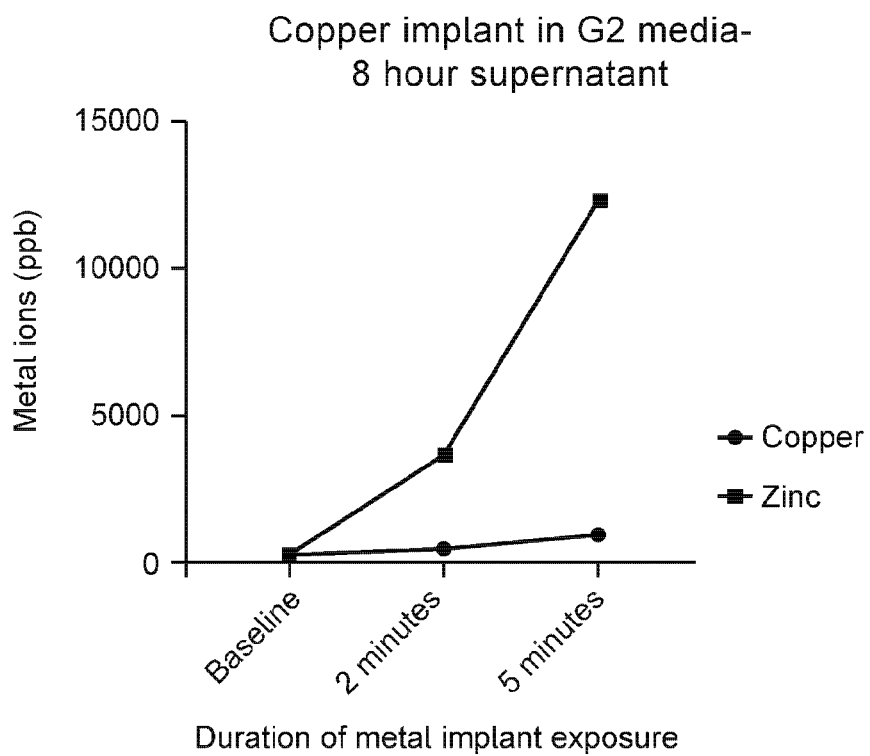
Figure 4A:
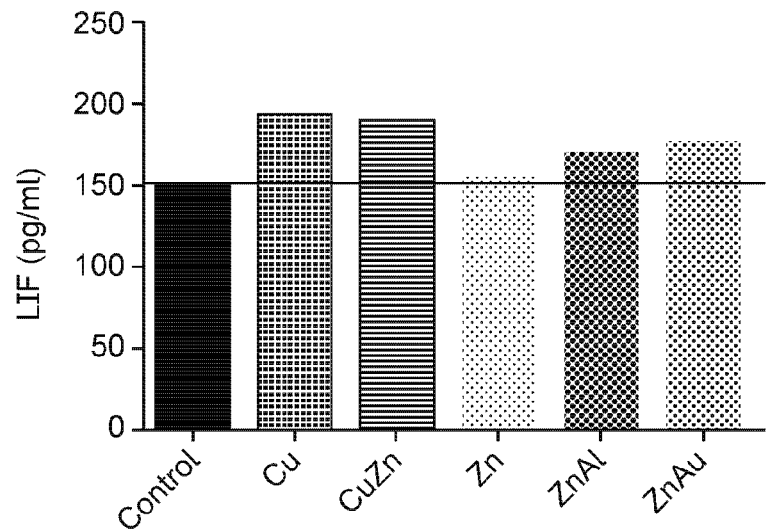
FIG. 4 provides graphical results showing the effect of metal ions released from various metal implants (i.e. a copper sheet implant (Cu), a copper-zinc sheet bimetal implant (CuZn), a zinc sheet implant (Zn), a zinc-aluminium sheet bimetal implant (ZnAl), and zinc-gold sheet bimetal implant (ZnAu)), on (A) LIF production and (B) VEGF-A production from Ishikawa cells. Measurements were taken from the culture supernatants following 8 hour cultures. The cells were exposed to the metal implants for 2 mins.
Figure 4B:
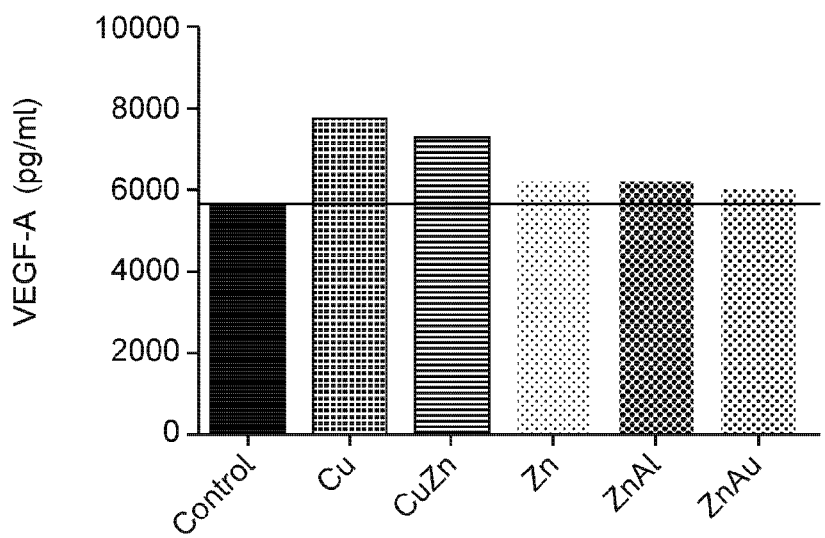

With the copper wire/copper sheet and CuZn bimetal sheet implants, mass spectroscopy confirmed the release of copper and zinc ions into conditioned αMEM/G2 medium over relatively short periods of time (see FIGS. 3A and 3B; nb. in the results obtained with the copper implant and shown in FIG. 3A, a small amount of zinc was detected due to the presence of zinc in the αMEM media). As expected, the presence of zinc (in the CuZn bimetal implant) slowed the release of copper ions into the solution (FIG. 3B), with zinc appearing to act as a sacrificial anode. In addition, it was observed that, like the $CuCl_2$ and $ZnCl_2$ solutions, the copper ions and zinc ions from the wire and sheet metal implants increased endometrial cell culture production of LIF and VEGF in multiple replicates (FIGS. 4A and 4B). The response was considerably better for copper or copper-zinc implants than for any of the other metal combinations.

Figure 5A:
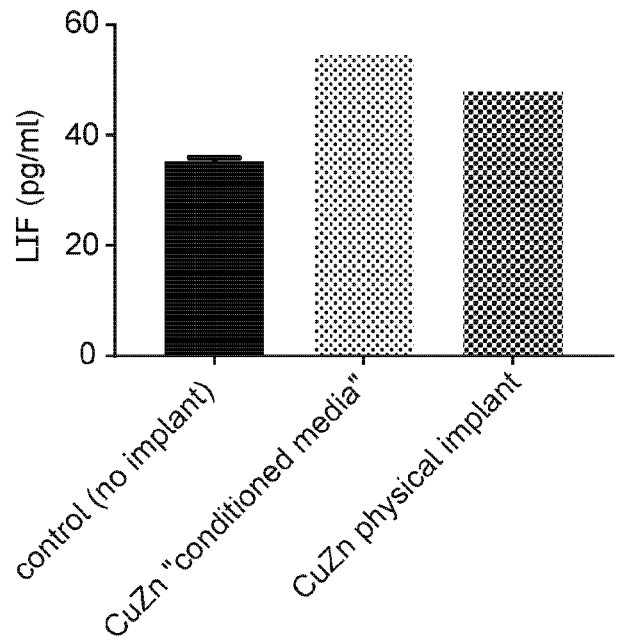
FIG. 5 provides graphical results contrasting the stimulation of (A) LIF production and (B) VEGF production from Ishikawa cells cultured in "conditioned media" (i.e. including copper and zinc ions); the experiment for LIF production also included a positive control where Ishikawa cells were cultured in culture media with a 2 minute exposure to a copper-zinc sheet bimetal implant (CuZn)
Figure 5B:
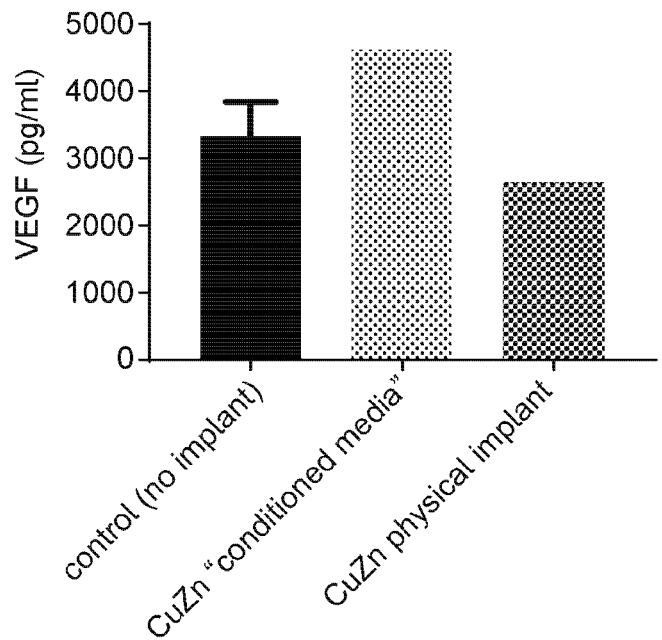
Figures 6A, 6B:
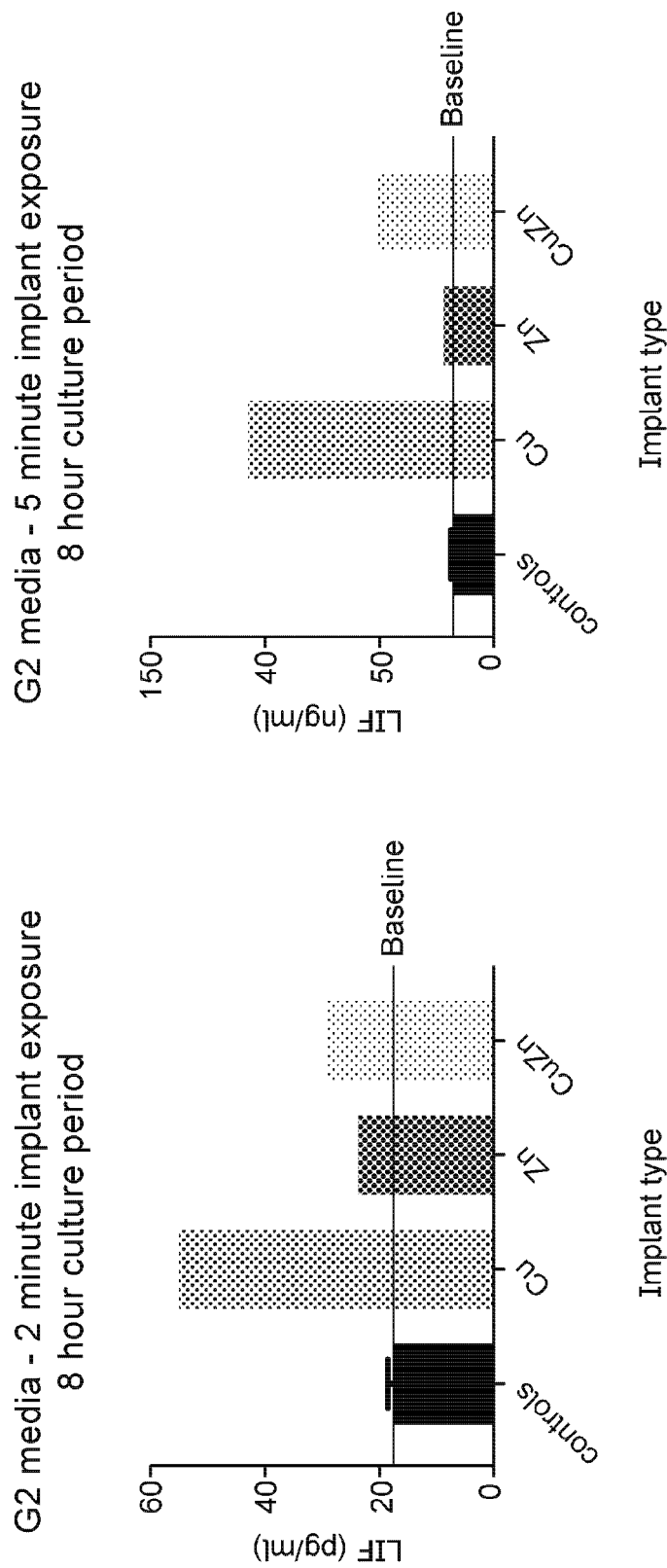
FIG. 6 provides graphical results obtained following 8 hour cultures of Ishikawa cells with 2 and 5 min exposures to metal implants (namely, a copper sheet implant (Cu), a zinc sheet implant (Zn), and a copper-zinc sheet bimetal implant (CuZn)). The graphs show the effect of the metal implant exposures on LIF production (A, B) and VEGF production (C, D)
Figure 6C:
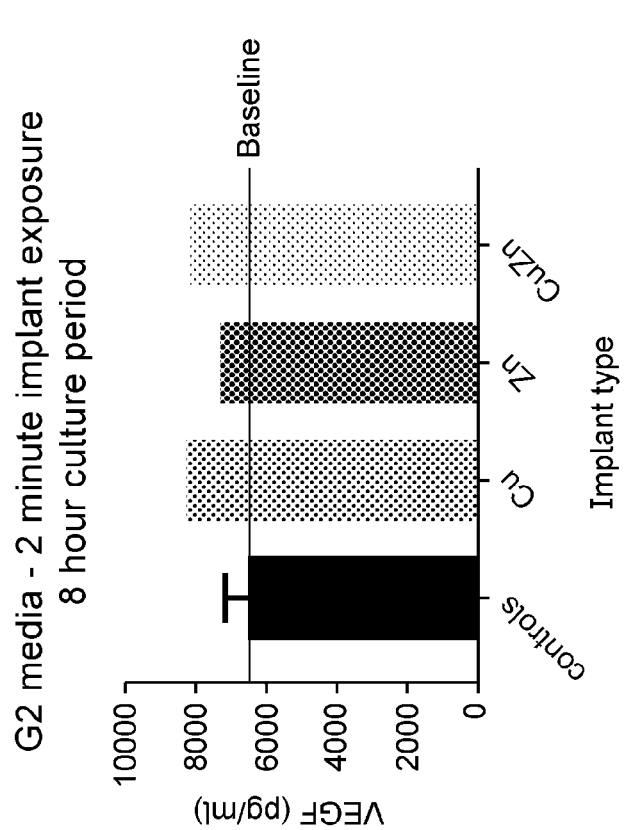
Figure 6D:
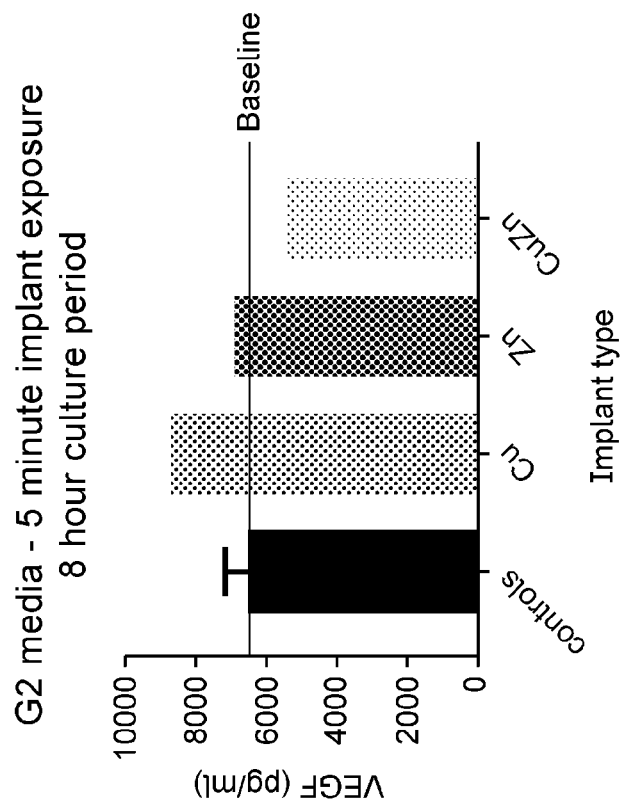

Further experiments were conducted to determine whether this increase (i.e. up-regulation) of LIF and VEGF production was related to the release of metal ions, the associated creation of a galvanic current during in situ corrosion or the physical presence of the metal implant ("foreign body" reaction). These experiments involved adding 1.5 ml of Ishikawa αMEM medium to each well of 2-well chamber slides without cells and thereafter adding CuZn bimetal implants for a period of 2 minutes (after which time they were removed using sterile tweezers). The resultant "conditioned media" was then added to 2-well slides containing Ishikawa cells and incubated for a period of 8 hours, thereby exposing these cells to metal ions but not the physical presence of the implant or any galvanic electrical current created by corrosion of the implant. These experiments revealed that conditioned media containing copper ions and zinc ions was still capable of eliciting an increase in LIF and VEGF production above that seen in control unexposed cultures (see FIGS. 5A and 5B).

Example 2

Effect of Metal Ions on Embryo Development and Attachment

Materials and Methods

Ishikawa cells were seeded onto 2-well chamber slides in Ishikawa medium until they reached 80-90% confluence. Then, 5 minutes prior to exposure to metal implants, the medium was changed to G2 embryo culture medium, and the Ishikawa cells exposed to copper, zinc or copper-zinc bimetal implants for either 2 or 5 minutes duration (or remained unexposed (control)), and the resulting G2 culture media collected 8 hours later. The supernatants were then analysed as described above in Example 1 to confirm that the metal implant exposure resulted in an up-regulation in endometrial LIF and VEGF production (see FIGS. 6A-D).

To determine whether metal ions were capable of enhancing embryo implantation, post-compaction mouse embryos were exposed to the "conditioned media" prior to undergoing outgrowth assays. In particular, pronucleate oocytes were collected from superovulated female F1 mice ~21-22 hours post-hCG. Following cumulus cell removal, oocytes were cultured in 20 µl drops (10 embryos/drop) of G1 medium under paraffin oil (Vitrolife) at 37° C. in 6% $CO_2$, 5% $O_2$ and 89% $N_2$. After 48 hours, compacting and morulae stage embryos were randomly transferred to culture in either (i) control G2 medium (Vitrolife) that had not been exposed to Ishikawa cells; (ii) individual culture in 2 µl of control, Ishikawa exposed G2; or (iii) individual culture in 2 µl drops of 2 minute copper-zinc bimetal implant exposed G2 medium. After 48 hours, the capacity of blastocysts to undergo outgrowth was assessed in the following manner. First, flat bottomed 96-well tissue culture plates (BD Biosciences, Franklin Lakes, NJ, United States of America) were coated with fibronectin (10 µg/ml; BD Biosciences), rinsed twice with sterile PBS and incubated with 4 mg/ml bovine serum albumin (Sigma-Aldrich). Wells were then rinsed before being filled with G2 medium supplemented with 5% FCS and equilibrated at 37° C. under paraffin oil (Ovoil; Vitrolife) for 3 hours prior to the addition of blastocysts. Hatched and hatching blastocysts from each respective treatment were placed into prepared wells (1 embryo per well) and incubated for 90 hours. During the culture period, outgrowths were examined and images taken at 66 and 90 hours post-transfer to the outgrowth plate with an inverted microscope (Nikon Eclipse TS100-F) equipped with a heated stage set at 37° C. The extent of outgrowth for each treatment was obtained by measuring the area of outgrowth in each of the images taken across the experiment using ImageJ. All images were collected and analysed at matching magnification.

Results and Discussion

Figure 7:
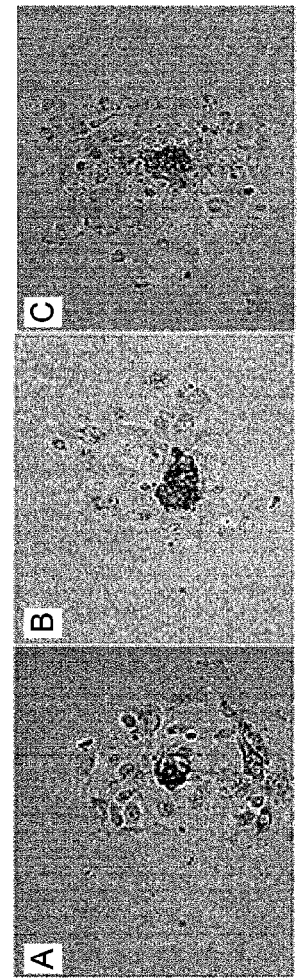
FIG. 7 provides examples of images showing embryo implantation outgrowth following culture of the day 3 murine embryos in: (A) fresh G2 media (control), (B) G2 media that had been conditioned by Ishikawa cell culture, and (C) G2 media that had been conditioned by Ishikawa cell culture with a two minute exposure to a copper-zinc bimetal implant.
Figure 8A:
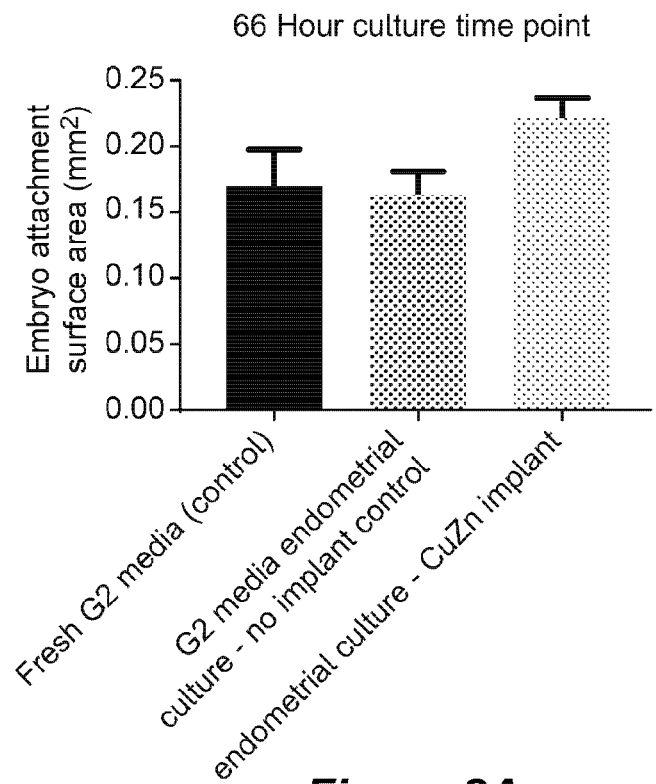
FIG. 8 shows the results of the extent of embryo implantation outgrowth (embryo attachment surface area, $mm^2$) following culture of the day 3 murine embryos in: fresh G2 media (control), G2 media that had been conditioned by Ishikawa cell culture, and G2 media that had been conditioned by Ishikawa cell culture with a two minute exposure to a copper-zinc bimetal implant. The results were assessed at 66 hour (A) and 90 hour (B) time points.
Figure 8B:
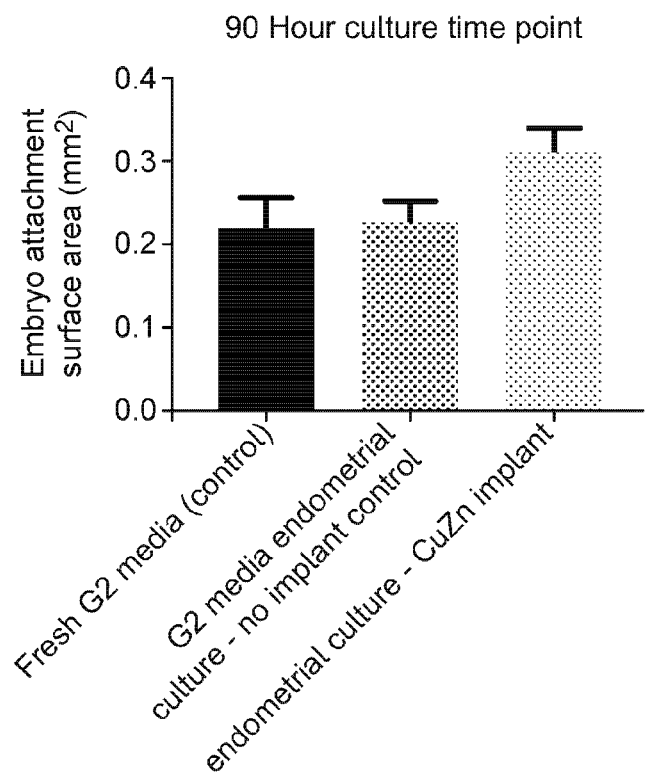

While no difference in the rate of embryo development was observed when the conditioned medium from the copper and zinc ion-exposed cultures was added to murine day 3 embryos, there was a very significant increase in the surface area of trophoblast outgrowth to the fibronectin-coated plates 3-4 days later (see FIGS. 7, 8A and 8B), thereby signifying improved embryo health and implantation potential.

This latter observation is important for two reasons. First, it confirms the ability of copper ions and zinc ions to mediate up-regulation of endometrial LIF/VEGF production to enhance implantation processes. Secondly, it confirms that while copper ions and zinc ions have traditionally been perceived as toxic to pre-implantation embryo development (Brinster and Cross, 1972; Webb et al., 1973; Holland and Pike 1978; Erbach et al., 1995), this toxicity was not significant with the short term exposure in these experiments. Therefore, despite nearly half a century of teaching suggesting that copper or zinc containing IUCDs provide effective contraception (Stanford, 2002), it is clear from the results described herein that short term delivery of copper ions and/or zinc ions to the endometrium can actually enhance the implantation processes.

While not wishing to be bound by theory, it is considered that the discrepancy observed between the experimentation described herein showing a beneficial effect of copper on endometrial function (in terms of LIF/VEGF production) and the well described detrimental effect of copper on endometrial health and function in IUCD users, may be explained by the considerable difference in the "dose" of copper delivered to the endometrium. That is, multiple studies have examined the rate of copper delivery in IUCD users, with this rate varying depending on the surface area of copper in the IUCD device and the time since initial insertion. In one such study, the average amount of copper delivered to the uterus was reported to vary from between 13.3 µg and 116.7 µg per day (Timonen, 1976). Other studies have reported mean rates of delivery as 26.7 µg (Chantler et al., 1984), 14 µg (Larsson et al., 1981) and 45 µg of copper per day (Hagenfeldt, 1972). In the experimentation of Example 1, a 4-fold increase in endometrial LIF production was observed at a $CuCl_2$ concentration of 200 µM. If it is assumed that the uterine cavity of a woman has a volume of approximately 150 µl (Casslen, 1986), the corresponding amount of copper that would need to be applied in vivo to give a dose equivalent to 200 µM would be 1.91 µg of copper. Further, as a relative decline in endometrial VEGF production was observed at a $CuCl_2$ concentration exceeding 100 µM in vitro (FIG. 2A), it is possible that the optimal quantum of copper needed to elicit a positive endometrial response in vivo is closer to 1 µg, a level approximating only 1-7% of the amount of copper IUCD users are exposed to daily (Hagenfeldt, supra; Timonen, supra; Larsson et al., supra; Chantler et al., supra). As such, it is considered that the dose of copper required to elicit a beneficial endometrial response (i.e. an increase in LIF/VEGF) that can enhance embryo implantation must be below 13.3 µg, the lowest reported rate of copper released per day by an IUCD device capable of impairing implantation (Copper T 100 $mm^2$ IUCD; Timonen, supra). In the experimentation of Example 1, 20 µM of $CuCl_2$ was the lowest amount of copper confirmed to elicit an increase in endometrial LIF and VEGF, which equates to an in vivo uterine delivery dose of 0.191 µg of copper. Thus, in some preferred embodiments of the methods of the present disclosure, the formulation/device would be administered/inserted to the subject so as to deliver a dose of copper between 0.1 µg and 10 µg to the uterine cavity. A similar dose range may also be preferred for zinc.

In addition to the up-regulation of endometrial LIF/VEGF production, copper ions and zinc ions may also enhance implantation processes by destroying harmful bacteria that may be present in the uterus. That is, while classically the uterus has been considered a sterile region devoid of potentially pathogenic bacteria, it is now recognised that colonisation of the endometrium with certain bacteria is seen in some infertile women and is associated with impaired implantation potential (Moreno et al., 2016). As both copper and zinc are known to possess anti-bacterial qualities (Vincent et al., 2016; Siddiqi et al., 2018), it is possible that the local application of copper ions or zinc ions (or in combination) to the uterine cavity may kill or inhibit these potentially implantation-impairing bacteria in this group of patients, thereby enhancing their natural and IVF assisted fertility potential.

Example 3

Prophetic Example of Treatment to Enhance Implantation of Transferred Embryo

An isotonic saline solution was prepared comprising $CuCl_2$ at a concentration of 150 µM and $ZnCl_2$ at 100 µM.

A 35 year-old woman who had experienced recurrent implantation failure (RIF), in particular five failed IVF cycles with good quality embryos, presented to the clinic 5 days ahead of an anticipated further transfer of an IVF embryo. Using a transfer catheter typically used for intra-uterine insemination therapy (e.g. Soft-Pass™ insemination catheter; Cook Medical Inc., Bloomington, IN, USA) loaded with a 200 µl amount of the $CuCl_2/ZnCl_2$ solution, the solution was administered to the uterine cavity.

On the scheduled day for embryo transfer, the woman re-presented to the clinic and received a good quality embryo in accordance with usual protocols.

Throughout the specification and the claims that follow, unless the context requires otherwise, the words "comprise" and "include" and variations such as "comprising" and "including" will be understood to imply the inclusion of a stated integer or group of integers, but not the exclusion of any other integer or group of integers.

The reference to any prior art in this specification is not, and should not be taken as, an acknowledgement of any form of suggestion that such prior art forms part of the common general knowledge.

It will be appreciated by those skilled in the art that the method(s), use(s) and/or formulation(s) of the present disclosure is not restricted in its use to the particular application described. Neither are the method(s), use(s) and/or formulation(s) restricted in their preferred embodiment(s) with regard to the particular elements and/or features described or depicted herein. It will also be appreciated that the method(s), use(s) and/or formulation(s) may be subject to numerous rearrangements, modifications and substitutions without departing from the scope of the present disclosure as set forth and defined by the following claims.

REFERENCES

Alfer J et al., *Geburtshilfe Frauenheilkd* 77(7):756-764 (2017).
Ametzazurra A et al., *Hum Reprod* 24(4):954-965 (2009).
Binder N K et al., *Hum Reprod* 29(10):2278-2286 (2014).
Boudjenah R et al., *J Assist Reprod Genet* 29(12):1415-1420 (2012).
Boudjenah R et al., *PLoS One* 9(9):e108287 (2014).
Brinster R L, Cross P C., *Nature* 238(5364):398-399 (1972).
Casslén B. *J Reprod Med* 31(6):506-510 (1986).
Chantler E N et al., *Br J Obstet Gynaecol* 91(2):172-181 (1984).
Charnock-Jones D S et al., *J Reprod Fertil* 101(2):421-426 (1994).
Chen J R et al., *Endocrinology* 141(12):4365-4372 (2000).
Cheng J et al., *Endocrinology* 158(6):1916-1928. doi: 10.1210/en.2017-00103 (2017).
Choi et al., *PLoS One* 11(6):e0157696. doi: 10.1371/journal.pone.0157696 (2016).
Cullinan E B et al., *Proc Natl Acad Sci USA* 93(7):3115-3120 (1996).
Dahdouh E M et al., *Reprod Biomed Online* 30(3):281-289 (2015).
Erbach G T et al., *Hum Reprod* 10(12):3248-3254 (1995).
Ghosh D, Sengupta J. *Contraception* 71(4):294-301 (2005).
Güney M et al., *Eur J Contracept Reprod Health Care* 12(3):212-219 (2007).
Hagenfeldt K. *Contraception* 6(1):37-54 (1972).
Hannan N J et al., *Endocrinology* 152(12):4948-4956 (2011).
Holland M K, Pike I L., *J Reprod Fertil* 53(2):335-339 (1978).
Jee B C et al., *Fertil Steril* 91(2):528-534 (2009).
Jinno M et al., *Fertil Steril* 76(6):1168-1174 (2001).
Karimzade M A et al., *Arch Gynecol Obstet* 281(3):499-503 (2010).
Kasius A et al., *Hum Reprod Update* 20(4):530-541 (2014).
Kelly W A et al., *J Reprod Fertil* 19(2):331-340 (1969).
Lalitkumar S et al., *Fertil Steril* 100(4):1160-1169. doi: 10.1016/j.fertnstert.2013.06.023 (2013).
Larsson B et al., *Fertil Steril* 36(6):734-736 (1981).

Lavranos T C et al., *J Reprod Fertil* 105(2):331-338 (1995).
Liang Y et al., *Mediators Inflamm* doi: 10.1155/2015/757184 (2015).
Mao X et al., *Fertil Steril* 108(1):55-61.e1. doi:10.1016/j.fertnstert.2017.05.014 (2017).
Martin J S et al., *Fertil Steril* 64(1):98-102 (1995).
Mikolajczyk M et al., *Am J Reprod Immunol* 58(1):65-74 (2007).
Mitchell M H et al., *Biol Reprod* 67(2):460-464 (2002).
Miwa I et al., *Fertil Steril* 91(4):998-1004 (2009).
Moreno I et al., *Am J Obstet Gynecol* 215(6):684-703 (2016).
Nastri C O et al., *Cochrane Database Syst Rev* 3:CD009517 (2015).
Norwitz E R et al., *N Engl J Med* 345(19):1400-1408 (2001).
Rafi A et al., *Indian J Clin Biochem* 28(2):147-151. doi: 10.1007/s12291-012-0240-9 (2013).
Robertson S A, Sharkey D J. *Fertil Steril* 106(3):511-519. doi: 10.1016/j.fertnstert.2016.07.1101 (2016).
Rockwell L C et al., *Biol Reprod* 67(6):1804-1810 (2002).
Sadovsky E et al., *Contraception* 12(5):541-547 (1975).
Schjenken J E, Robertson S A., *Reprod Domest Anim* 49 Suppl 3:27-36. doi: 10.1111/rda.12383 (2014).
Sengupta J et al., *Contraception* 74(5):419-425 (2006).
Seo W S et al., *Fertil Steril* 95(8):2707-2710 (2011).
Sheppard B L., *Contraception* 36(1):1-10 (1987).
Siddiqi K S et al., *Nanoscale Res Lett* 13(1):141 (2018).
Sigalos G et al., *Hum Fertil* (Camb) 20(1):3-13 (2017).
Stanford J B, Mikolajczyk R T. *Am J Obstet Gynecol* 187(6):1699-1708 (2002).
Stewart C L et al., *Nature* 359(6390):76-79 (1992).
Timonen H. *Contraception* 14(1):25-38 (1976).
Valbuena D et al., *Fertil Steril* 108(1):4-8. doi:10.1016/j.fertnstert.2017.05.030 (2017).
Vincent M et al., *Int J Hyg Environ Health* 219(7 PtA):585-591 (2016).
Webb F T. *J Reprod Fertil* 32(3):429-439 (1973).
Wu J et al., *Contraception* 85(5):509-518. doi: 10.1016/j.contraception.2011.09.016 (2012).
Yuan X et al., *Reprod Biomed Online* 33(2):197-205 (2016).
Xin Z M et al., *Zhonghua Fu Chan Ke Za Zhi* 39(11):771-775 (2004).
Zipper J et al., *Int J Fertil* 22(3):155-161 (1977).

The invention claimed is:

1. A method of enhancing embryo implantation in a subject, wherein the method comprises administering to a uterine cavity of the subject a formulation comprising copper, wherein the copper is provided in solution or gel form,
 (i) wherein the subject is hoping to achieve pregnancy through natural conception, and the formulation is administered to the subject in the same menstrual cycle prior to ovulation, or
 (ii) wherein the subject is undergoing treatment by assisted reproductive technology involving the transfer of embryo, and the formulation is administered to the subject in the same menstrual cycle prior to embryo transfer, or
 (iii) wherein the subject is undergoing treatment by intra-uterine insemination (IUI), and the formulation is administered to the subject in the same menstrual cycle prior to IUI,
 wherein the formulation is administered to the uterine cavity of the subject in an amount effective to stimulate endometrial production of leukaemia inhibitory factor (LIF) and vascular endothelial growth factor (VEGF), wherein the copper is provided to the uterine fluid cavity for a period no longer than 60 minutes.

2. The method according to claim 1, wherein the formulation comprises copper in a form such that it provides a source of copper ions within the uterine cavity.

3. The method according to claim 1, wherein the copper is provided in a biodegradable gel form or in a form which provides an in situ biodegradable form within the uterine cavity.

4. The method according to claim 3, wherein the copper is formulated with hydroxyethyl cellulose and glycerol.

5. The method according to claim 1, wherein the solution is a salt of copper.

6. The method according to claim 1, wherein the formulation provides copper ions to the uterine fluid cavity in an amount in the range of about 0.025 µg to about 12.5 µg per dose.

7. The method according to claim 1, wherein the formulation provides copper ions to the uterine fluid cavity in an amount of at least 1250 ppb.

8. The method according to claim 1, wherein the formulation comprises 20-200 µM copper ions.

9. The method of claim 1, wherein the formulation is administered to the subject no more than 14 days prior to the embryo transfer.

10. The method of claim 1, wherein the formulation is administered to the subject between the cessation of menses and commencement of the increase in progesterone that accompanies ovulation.

11. The method according to claim 1, wherein the method comprises inserting into the uterine cavity of the subject a device comprising the formulation comprising copper for a period of time that is effective to stimulate endometrial production of leukaemia inhibitory factor (LIF) and vascular endothelial growth factor (VEGF).

12. The method according to claim 11, wherein the device has an elongated form and comprises a distal section and a proximal base section, and the step of inserting the device into the uterine cavity involves inserting at least a portion of the distal section into the uterine cavity.

13. The method according to claim 12, wherein the portion of the distal section that is inserted into the uterine cavity, or a part thereof, may comprise or be provided with copper and may elicit copper ions to stimulate endometrial production of LIF and VEGF.

14. The method according to claim 1, wherein the formulation is administered on multiple occasions per day or over a series of days in the same menstrual cycle.

* * * * *